US006677357B2

(12) United States Patent
Zhu et al.

(10) Patent No.: US 6,677,357 B2
(45) Date of Patent: Jan. 13, 2004

(54) RAPAMYCIN 29-ENOLS

(75) Inventors: Tianmin Zhu, Monroe, NY (US); Mahdi B. Fawzi, Morristown, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/224,971

(22) Filed: Aug. 22, 2002

(65) Prior Publication Data

US 2003/0114477 A1 Jun. 19, 2003

Related U.S. Application Data

(60) Provisional application No. 60/314,211, filed on Aug. 22, 2001.

(51) Int. Cl.[7] ............... A61K 31/445; C07D 401/00; C07D 405/00; C07D 409/00
(52) U.S. Cl. ........................... 514/326; 546/207
(58) Field of Search ..................... 546/207; 514/326

(56) References Cited

U.S. PATENT DOCUMENTS

| | | | |
|---|---|---|---|
| 3,929,992 A | 12/1975 | Sehgal et al. | 424/122 |
| 3,993,749 A | 11/1976 | Sehgal et al. | 424/122 |
| 4,401,653 A | 8/1983 | Eng et al. | 424/122 |
| 4,885,171 A | 12/1989 | Surendra et al. | 424/122 |
| 5,078,999 A | 1/1992 | Warner et al. | 424/122 |
| 5,080,899 A | 1/1992 | Sturm et al. | 424/122 |
| 5,100,899 A | 3/1992 | Calne et al. | 424/122 |
| 5,206,018 A | 4/1993 | Sehgal et al. | 424/122 |
| 5,286,730 A | 2/1994 | Caufield et al. | 514/291 |
| 5,286,731 A | 2/1994 | Caufield et al. | 514/291 |
| 5,288,711 A | 2/1994 | Mitchell et al. | 514/56 |
| 5,321,009 A | 6/1994 | Baeder et al. | 514/4 |
| 5,362,718 A | 11/1994 | Skotnicki et al. | 514/63 |
| 5,387,589 A | 2/1995 | Kulkarni et al. | 514/291 |
| 5,496,832 A | 3/1996 | Armstrong et al. | 514/291 |
| 5,516,781 A | 5/1996 | Morris et al. | 514/291 |
| 5,561,138 A | 10/1996 | Armstrong | 514/291 |
| 6,002,008 A | 12/1999 | Wissner et al. | 546/60 |
| 6,277,983 B1 | 8/2001 | Shaw et al. | 540/456 |
| 2003/0100577 A1 | 5/2003 | Zhu et al. | 514/291 |

FOREIGN PATENT DOCUMENTS

| | | |
|---|---|---|
| EP | 0 378 318 | 7/1990 |
| EP | 0 525 960 B1 | 3/1996 |
| GB | 2 247 456 | 3/1992 |
| WO | WO 96/17816 | 6/1996 |
| WO | WO 96/17845 | 6/1996 |
| WO | WO 98/09970 | 3/1998 |

OTHER PUBLICATIONS

Vezina et al., The Journal of Antibiotics, 28(10), 721–726 (1975).
Sehgal et al., The Journal of Antibiotics, 28(10), 727–732 (1975).
Baker, et al., The Journal of Antibiotics, 31(6), 539–545 (1978).
Calne et al., The Lancet, 1183–1185 (1978).
Martel et al., Can. J. Physiol. Pharmacol. 55, 48–51 (1977).
Staruch et al., The FASEB Journal, 3(3) 1989.
Dumont et al., The FASEB Journal, 3(4) 1989.
Steiner, J.P. et al., Nature Medicine, vol. 3, No. 4, Apr. 1997, pp. 421–428.
Dickman, D.A. et al., Bioorganic & Medicinal Chemistry, vol. 10, 2000, pp. 1405–1408.
Sedrani, R. et al., Bioorganic & Medicinal Chemistry, vol. 9, 1999, pp. 459–462.
Holt, Denois A. et al., Bioorganic & Medicinal Chemistry Letters, vol. 13, No. 10, 1993, pp. 1977–1980.
Parker et al, Rapamycin, but Not FK506 and GPI–1046, Increases Neurite Outgrowth in PC12 Cells by Inhibiting Cell Cycle Progression, Neuropharmacology 39, pp. 1913–1919, (2000).
Adalsteinsson et al, Generation and Evaluation of Putative Neuroregenerative Drugs. Part 1.: Virtual Point Mutations to the Polyketide Rapamycin, Bioorganic & Medicinal Chemistry 8, pp. 617–624 (2000).
Adalsteinsson et al, Generation and Evaluation of Putative Neuroregenerative Drugs. Part 2: Screening Virtual Libraries of Novel Polyketides Which Possess the Binding Domain of Rapamycin, Bioorganic & Medicinal Chemistry 8, pp. 625–635 (2000).

*Primary Examiner*—Bruck Kifle
(74) *Attorney, Agent, or Firm*—Howson and Howson; Arnold Milowsky

(57) ABSTRACT

This invention provides non-immunosuppressive rapamycin 29-enols, which are useful as neurotrophic agents, in the treatment of solid tumors, and vascular disease.

10 Claims, No Drawings

RAPAMYCIN 29-ENOLS

This application claims priority from copending U.S. provisional application Ser. No. 60/314,211, filed Aug. 22, 2001, the entire disclosure of which is hereby incorporated by reference.

BACKGROUND OF THE INVENTION

This invention relates to non-immunosuppressive rapamycin 29-enols, which are useful as neurotrophic agents, in the treatment of solid tumors, and vascular disease.

Rapamycin is a macrocyclic triene antibiotic produced by *Streptomyces hygroscopicus*, which was found to have antifungal activity, particularly against *Candida albicans*, both in vitro and In vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies. FK-506 and some synthetic FKBP-12 binding ligands have been shown to be neuroprotective and neuroregenerative [U.S. Pat. Nos. 5,696,135, 5,721,256, 5,780,484, 5,811,434 and 5,840,736].

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], anemia [U.S. Pat. No. 5,561,138] and increase neurite outgrowth [Parker, E. M. et al, Neuropharmacology 39, 1913–1919, 2000].

A rapamycin ester, rapamycin 42-ester with 3-hydroxy-2-(hydroxymethyl)-2-methylpropionic acid [disclosed in U.S. Pat. No. 5,362,718], also known as CCI-779, has been shown to have antitumor activity against a variety of tumor cell lines, in in vivo animal tumor models, and in Phase I clinical trials. [Gibbons, J., Proc. Am. Assoc. Can. Res. 40:301 (1999); Geoerger, B., Proc. Am. Assoc. Can. Res. 40:603 (1999); Alexandre, J., Proc. Am. Assoc. Can. Res. 40:613 (1999); and Alexandre, J., Clin. Cancer. Res. 5 (November Supp.): Abstr. 7 (1999)].

DESCRIPTION OF THE INVENTION

This invention provides non-immunosuppressive rapamycin 29-enols, and methods of using them that are described herein. As defined herein, the term "a rapamycin 29-enol" defines a class of neurotrophic compounds which contain the basic rapamycin 29-enol nucleus (shown below). These compounds lack the immunosuppressive properties associated with an intact rapamycin nucleus. The rapamycin 29-enols of this invention include compounds which may be chemically or biologically modified as derivatives of the rapamycin 29-enol nucleus, while still retaining neutrophic properties. Accordingly, the term "a rapamycin 29-enol" includes esters, ethers, oximes, hydrazones, and hydroxylamines of rapamycin, as well as rapamycin 29-enols in which functional groups on the rapamycin 29-enol nucleus have been modified, for example through reduction or oxidation. The term "a rapamycin 29-enol" also includes pharmaceutically acceptable salts of rapamycin 29-enols, which are capable of forming such salts, either by virtue of containing an acidic or basic moiety.

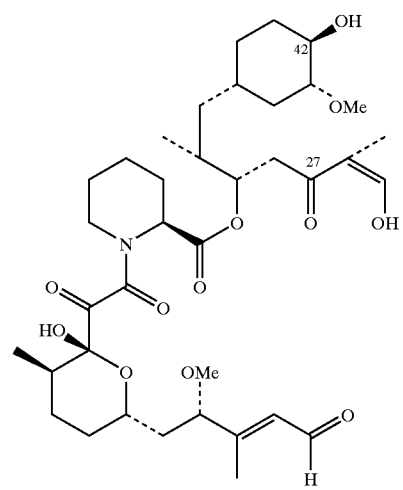

RAPAMYCIN 29-ENOL

It is preferred that the esters and ethers of rapamycin 29-enol are of the hydroxyl groups at the 42-position of the rapamycin 29-enol nucleus, and that the oximes, hydrazones, and hydroxylamines are of a ketone at the 42-position (following oxidation of the 42-hydroxyl group) and of 27-ketone of the rapamycin 29-enol nucleus.

Preferred 42-esters and ethers of rapamycin, which serve as starting materials for the corresponding rapamycin 29-enolss, are disclosed in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers are disclosed in the patents listed above. The preparation of the corresponding esters and ethers of rapamycin 29-enols can be accomplished using the methodology described in these patents, starting with rapamycin, followed by the ring opening reactions described herein. An improved synthesis of 42-esters and ethers of rapamycin is disclosed in U.S. Pat. No. 6,277,539, which is hereby incorporated by reference.

Preferred oximes, hydrazones, and hydroxylamines of rapamycin are disclosed in U.S. Pat. Nos. 5,373,014, 5,378,836, 5,023,263, 5,023,264, and 5,563,145, which are hereby incorporated by reference. The preparation of these oximes, hydrazones, and hydroxylamines, which serve as starting materials for the corresponding rapamycin 29-enols, are disclosed in the above listed patents. The preparation of the corresponding oximes, hydrazones, and hydroxylamines of rapamycin 29-enol can be accomplished using the methodology described in these patents, starting with rapamycin, followed by the ring opening reactions described herein.

Particularly preferred rapamycin 29-enols include rapamycin 29-enol, rapamycin 29-enol 42-ester with 3-hydroxy-2-(hydroxymethyl)-2-methylpropionic acid [see U.S. Pat. Nos. 5,362,718 and 6,277,539 for the preparation of rapamycin 42-ester with 3-hydroxy-2-(hydroxymethyl)-2-methylpropionic acid], and 42-O-(2-hydroxy)ethyl rapamycin 29-enol [see U.S. Pat. No. 5,665,772 for the preparation of 42-O-(2-hydroxy)ethyl rapamycin].

When applicable, pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when the rapamycin contains a suitable basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when the rapamycin contains a suitable acidic moiety.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

The compounds of this invention can be made from a rapamycin using commercially available starting materials or from starting materials that can be prepared according to literature procedures. The desired rapamycin 29-enol can be prepared by the treatment of the rapamycin with ozone by monitoring the progress of the reaction, until the desired product has formed. In addition to the production of the rapamycin 29-enol, corresponding rapamycin dialdehydes are also produced during the ozonolysis oxidation. The structure of rapamycin dialdehyde is provided below.

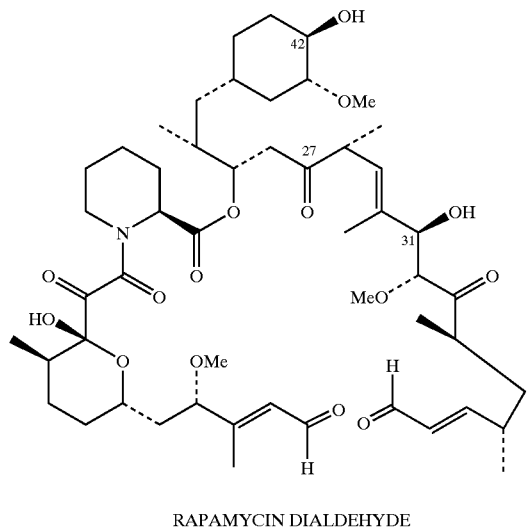

RAPAMYCIN DIALDEHYDE

Additionally, during the ozonolysis of the rapamycin, (2E,4S,6R)-6-[(5S,6R)-5-hydroxy-6-methoxy-4-methyl-2,3,7-trioxabicyclo[2.2.1]hept-1-yl]-4-methylhept-2-enal, having the structure shown below was produced (Example 3).

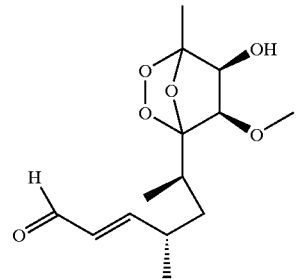

The neuroregeneration activity for the compounds of this invention was confirmed in a standard pharmacological test procedure by evaluating rapamycin dialdehyde (Example 1) and rapamycin 29-enol (Example 2), as representative compounds of this invention, against SH-SY5Y cells in vitro [Gold et al., Exp Neurol 147:269–278, 1997]. Briefly, SH-SY5Y cells were placed in 6-well plate treated with aphidicolin for 5 days followed by the test compounds using 6-well plates. For controls, wells were untreated, or treated with nerve growth factor (NGF) alone. Test wells were treated with NGF plus Example 1 and Example 2, or rapamycin. Cells were photographed at 168 hours. Analysis of neuritic lengths was performed on photographic prints using a Houston Instrument HI-PAD digitizing tablet connected to an IBM XT computer with appropriate software (Bioquant IV, R&M Biometrics, Nashville, Tenn.). Mean values for axonal areas were compared using by ANOVA (STATVIEW, Abacus Concepts, Inc., Berkeley, Calif.). The following table summarizes the results that were obtained.

TABLE I

Mean Neurite Lengths after 168 h

|  | Neurite Length (μm) |
|---|---|
| Untreated Cell | 109.5 ± 2.6[a] (n = 115) |
| NGF | 196.5 ± 7.7* (n = 112) |
| Rapamycin + NGF | 261.4 ± 13.1** (n = 119) |
| Example I + NGF | 229.8 ± 9.5** (n = 141) |
| Example II + NGF | 239.7 ± 10.0** (n = 155) |

[a]Values are mean ± SEM (in μm).
n, number of cells.
*p < 0.05 compare to Untreated Cell
**p < 0.05 compare to NGF and Untreated Cell The results obtained in the standard pharmacological test procedure demonstrated that the compounds of this invention are useful as neurotrophic agents, and are particularly useful in promoting promote neuronal regeneration and functional recovery and to stimulate neurite outgrowth and thereby to treat various neuropathological states, including damage to peripheral nerves and the central nervous system caused by physical injury (e.g., spinal cord injury and trauma, sciatic or facial nerve lesion or injury), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, dimentia, Alzheimer's disease, Parkinson's disease, and Huntington's chorea.

Antineoplastic activity for the compounds of this invention was confirmed by evaluating the antineoplastic activity of representative compounds of this invention (Examples 1–5) against six tumor cell lines in vitro. Briefly, tumor cells from six cell lines were placed in wells of a 96 well microtiter plate. The following tumor cell lines were used: 3T3 (ovarian), 3T3/H2N (ovarian—resistant to cis-platin), A431 (vulva epidermoid origin), SW620 (colon), SKBR3 (breast), and MDA-435 (breast). The tumors cells were grown in the presence of serial dilutions of the compound to be evaluated for 48 hours, and cell growth determined using a calorimetric procedure (sulforhodamine B). The inhibition of growth was calculated compared to the number of cells at the time of test compound addition. Results are expressed as an $IC_{50}$ (μg/ml); and are provided in Table 2.

TABLE 2

Antineoplastic Activity ($IC_{50}$ in μg/ml)

| Cell line | Example I | Example II | Example III | Example IV | Example V |
|---|---|---|---|---|---|
| 3T3 | 0.72 | >5 | 4.11 | 1.5 | >5 |
| 3T3/H2N | 0.68 | >5 | >5 | 0.72 | 4.96 |
| A431 | 0.91 | >5 | 3.01 | 2.64 | >5 |
| SKBR3 | 0.52 | >5 | 2.05 | 0.36 | 2.69 |
| MDA435 | 1.23 | >5 | 4.13 | 1.1 | >5 |
| SW620 | 1.41 | >5 | >5 | 3.04 | >5 |

The results of this standard pharmacological test procedure demonstrate that the compounds of this invention are useful as antineoplastic agents. In particular, the compounds of this invention are useful against solid tumors, including sarcomas and carcinomas; and more particularly against astrocytomas, prostate cancer, breast cancer, colon cancer, small cell lung cancer, and ovarian cancer; and adult T-cell leukemia/lymphoma.

The compounds of this invention are also useful in the treatment or inhibition of hyperproliferative vascular diseases such as restenosis.

When used for restenosis, it is preferred that the compounds of this invention are used to treat restenosis that occurs following an angioplasty procedure. When used for this treating restenosis following an angioplasty, the compounds of this invention can be administered prior to the procedure, during the procedure, subsequent to the procedure, or any combination of the above.

It is understood that the effective dosage of a rapamycin 29-enol may vary depending upon the particular compound utilized, the mode of administration, the condition, and severity thereof, of the condition being treated, as well as the various physical factors related to the individual being treated. As used in accordance with invention, satisfactory results may be obtained when the rapamycin 29-enol is administered in a daily oral dosage of from about projected daily dosages of active compound would be 0.1 μg/kg–100 mg/kg, preferably between 0.001–25 mg/kg, and more preferably between 0.01–5 mg/kg. The projected daily dosages are expected to vary with route of administration.

When the rapamycin 29-enol is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. It is more preferred that poloxamer 188 is used as the surface modifying agent. Oral formulations herein may utilize standard delay or time release formulations to alter the absorption of the active compound(s). Preferred oral formulations of rapamycin is disclosed in U.S. Pat. Nos. 5,559,121; 5,536,729; 5,989,591; and 5,985,325, which are hereby incorporated by reference.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred parenteral formulations for administering rapamycin are disclosed in U.S. Pat. Nos. 5,530,006; 5,516,770; and 5,616,588, which are hereby incorporated by reference.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

When the rapamycin 29-enol is used to treat or inhibit a hyperproliferative vascular disorder, such as restenosis, it is preferable that the rapamycin dialdehyde is provided via a vascular stent or shunt which has been coated or impregnated with the rapamycin 29-enol.

The following provides procedures for the preparation of representative compounds of this invention.

EXAMPLE 1 (METHOD A)

Rapamycin Dialdehyde

Rapamycin (5.0 g, 5.5 mmole) was dissolved in 100 mL dioxane and 35 mL water. Then 61 mg of $OsO_4$ was added and reaction was carried out at room temp. After stirred 30 min (solution became dark green). Sodium metaperiodate (2.34 g, 10.9 mmole) was added batch by batch in 30 min. The reaction was stirred overnight. The reaction was stopped by extracting reaction mixture by 200 mL $CH_2Cl_2$ and work-up to get 5.1 g of crude product (66% of total peak area for WAY-181340, 12% unreacted rapamycin). The crude product was purified by preparative HPLC on a Prep Nova-pak HR C18 column (300×19 mm) using gradient method that held 65% A and 35% B for the first 5 min then changed from 65% A and 35% B to 10% A and 90% B in 30 min. Buffer A is 90% water and 10% acetonitrile. Buffer B is 10% water and 90% acetonitrile. The flow rate is 20 mL/min. The fraction at 20–21 min was collected and extracted with methylene chloride. The organic layer was dried with anhydrous sodium sulfate. The organic solvent was removed using a rotary evaporation system. The residual was dissolved in 3 mL methylene chloride and precipitated by adding 15 mL hexane. After filtration, the white solid was dried in the speed-vac overnight. If the product is not pure enough, it was repurified by 51% B and 49% A on same column. The peak at 13 min was collected, work up again as described above. A white solid was obtained.

| | Assignments for Compound I, DMSO-d6, 400 MHz ($^{13}C$: 100 MHz) | | | | | |
|---|---|---|---|---|---|---|
| C# | $\delta\ ^{13}C$ major | $\delta\ ^{13}C$ minor | $\delta\ ^{1}H$ major | $\delta\ ^{1}H$ minor | $^{1}H$ Correltn | HMBC |
| 1 | 163.34 | | 6.91 | | 2, 36 | 3, 35, 36, 50 |
| 2 | 131.37 | | 6.12 | | 1, 3 | 3, 36 |
| 3 | 194.38 | | 9.52 | | 2 | 2 |
| 4 | 192.08 | 191.92 | 10.02 | | 5 | 5 |
| 5 | 127.54 | 128.07 | 6.06 | 6.00 | 4 | 4, 7, 45 |
| 6 | 160.98 | 161.23 | | | | |
| 7 | 81.78 | 81.87 | 3.78 | 3.76 | 8 | 5 |
| 8 | 39.41 | 39.08 | 1.62; 1.62 | | | |
| 9 | 65.97 | | 3.74 | | | |
| 10 | 32.81 | | 1.76 (eq) | | | |
| | | | 1.15 (ax) | | | |
| 11 | 26.33 | | 1.50 | | | |
| 12 | 34.68 | 34.49 | 2.00 | | | |
| 14 | 99.27 | 99.98 | | | | |
| 14 (OH) | | | 6.44 | 6.53 | | 12, 13, 15 |
| 15 | 198.98 | 199.45 | | | | |
| 16 | 166.06 | 166.89 | | | | |
| 18 | 43.42 | 37.94 | 3.51 (eq) | 4.22 (eq) | | |
| | | | 3.10 (ax) | 2.56 (ax) | | |
| 19 | 24.30 | | 1.63 (eq) | | | |
| | | | 1.27 (ax) | | | |
| 20 | 20.70 | | 1.75 | | | |
| 21 | 26.87 | | 2.14 (eq) | | | |
| | | | 1.64 (ax) | | | |
| 22 | 50.92 | 54.78 | 4.96 | 4.46 | | |
| 23 | 169.47 | 168.77 | | | | |
| 25 | 74.10 | | 5.17 | | 26, 37 | |
| 26 | 39.95 | | 2.72 | | | |
| | | | 2.67 | | | |

| | Assignments for Compound I, DMSO-d6, 400 MHz ($^{13}$C: 100 MHz) | | | | | |
|---|---|---|---|---|---|---|
| C# | δ $^{13}$C major | δ $^{13}$C minor | δ $^{1}$H major | δ $^{1}$H minor | $^{1}$H Correltn | HMBC |
| 27 | 208.15 | 208.37 | | | | |
| 28 | 45.51 | | 3.45 | | | |
| 29 | 126.06 | | 5.21 | | 28, 48(w) | |
| 30 | 138.00 | | | | | |
| 31 | 75.95 | | 4.01 | | 31-OH, 32 | |
| 31 (OH) | | | 5.26 | | 31 | 30, 32 |
| 32 | 86.04 | | 3.78 | | | |
| 33 | 212.53 | | | | | |
| 34 | 40.05 | | 2.80 | | | |
| 35 | 37.63 | | 2.56; 1.22 | | | |
| 36 | 33.85 | | 2.55 | | | |
| 37 | 32.55 | | 1.83 | | | |
| 38 | 38.08 | | 1.16; 1.02 | | | |
| 39 | 32.42 | | 1.32 | | | |
| 40 | 35.24 | 35.20 | 1.94 (eq) 0.62 (ax) | | | |
| 41 | 83.77 | | 2.83 | | | |
| 42 | 73.06 | | 3.19 | | | |
| 42 (OH) | | | 4.53 | | | |
| 43 | 32.81 | | 1.74 (eq) 1.22 (ax) | | | |
| 44 | 30.92 | | 1.59 (eq) 0.88 (ax) | | | |
| 45 | 11.82 | | 2.06 | | | |
| 46 | 15.61 | | 0.69 | | | |
| 47 | 15.70 | | 1.00 | | | |
| 48 | 11.38 | | 1.70 | | | |
| 49 | 15.29 | | 0.95 | | | |
| 50 | 19.76 | | 1.06 | | | |
| 51 | 15.06 | | 0.80 | | | |
| 52 | 55.93 | | 3.11 | | | |
| 53 | 57.55 | | 3.19 | | | |
| 54 | 56.57 | | 3.30 | | | |

The pseudo-molecular ions were observed with the [M−H]$^−$ ion at m/z 944 and [M+NH4]$^+$ ion at m/z 963 by negative and positive electrospray modes, respectively.

EXAMPLE 1 (METHOD B)

Rapamycin 42-dialdehyde

Rapamycin (1.0 g, 1.09 mmol) was dissolved in 250 mL CH$_2$Cl$_2$. The round bottom flask was put into a dry ice bath. The ozone gas was bubbling though the solution for 6 min (6 L/min, at output 7 of control knob setting). Then the reaction mixture was stirred 1 h. Methyl sulfide (100 μl) was added and the reaction was stirred for another 1 h. Reaction was stopped by adding 200 mL water into reaction mixture. About 0.97 g of crude product was obtained after work-up (off-white solid, 44% of total peak area for WAY-181340). LC/MS results prove that the major peak is WAY-181340.

EXAMPLES 2 AND 3

Rapamycin 29-enol (Example 2) and (2E,4S,6R)-6-[(5S,6R)-5-Hydroxy-6-methoxy-4-methyl-2,3,7-trioxabicyclo[2.2.1]hept-1-yl]-4-methylhept-2-enal (Example 3)

Rapamycin (1.3 g, 1.40 mmol) was treated same procedure as Example 1A except the ozone gas was bubbling for 50 min. About 1.1 g of crude product was obtained after work-up (off-white solid, 44% of total peak area for the dialdehyde of Example 2). Two major peaks (9.5 min and 14 min) were isolated by preparative HPLC. Example 2 (14 min) was obtained as white solid (50 mg) and Example 3 (9.5 min) was obtained as clear oil (23 mg).

| | Assignments for Example 2 in DMSO-d6 at 30° C., 400 MHz ($^{13}$C: 100 MHz) | | | |
|---|---|---|---|---|
| C# | δ $^{13}$C major | δ $^{13}$C minor | δ $^{1}$H major | δ $^{1}$H minor |
| 4 | 192.24 | 192.07 | 10.02 | 10.01 |
| 5 | 128.29 | 127.57 | 6.07 | 5.99 |
| 6 | 161.10 | 161.46 | | |
| 7 | 81.94 | 81.79 | 3.76 | 3.77 |
| 8 | 39.22 | 39.04 | 1.60; 1.60 | 1.74; 1.74 |
| 9 | 65.97 | 65.97 | 3.73 | 3.73 |
| 10 | 30.85 | 30.93* | 1.27 | 1.27 |
| 11 | 227.23 | 27.23 | 1.45 | 1.50 |
| 12 | 34.82 | 34.66 | 2.09 | 2.01 |
| 14 | 99.34 | 99.04 | | |
| 14 (OH) | | | 6.56 | 6.48 |
| 15 | 199.18 | 199.59 | | |
| 16 | 166.12 | 166.85 | | |
| 18 | 43.54 | 37.90 | 3.44 (eq) 3.13 (ax) | 4.16 (eq) 2.60 (ax) |
| 19 | 24.17 | 24.51 | 1.55 (eq) 1.34 (ax) | 1.59 (eq) 1.21 (ax) |
| 20 | | | | |
| 21 | 26.49 | 26.32 | 2.12 (eq) 1.58 (ax) | 2.08 (eq) 1.56 (ax) |
| 22 | 51.00 | 55.93 | 4.92 | 4.44 |
| 23 | 169.61 | 168.82 | | |
| 25 | 75.56 | 75.33 | 5.29 | 5.22 |
| 26 | 35.94 | 36.74 | 2.87 2.66 | 2.76 2.76 |
| 27 | 196.03 | 196.03 | | |
| 28 | 115.12 | 114.96 | | |
| 29 | 157.38 | 157.16 | 7.83 | 7.78 |
| 29-OH | | | 10.76 | 10.76 |
| 37 | 32.77 | 33.15 | 1.86 | 1.81 |
| 38 | 38.39 | 38.49 | 1.24 1.07 | 1.21 1.02 |
| 39 | 31.04 | 30.93* | 1.33 | 1.30 |
| 40 | 35.49 | 34.49 | 1.96 (eq) 0.64 (ax) | 1.94 (eq) 0.61 (ax) |
| 41 | 83.87 | 83.87 | 2.83 | 2.81 |
| 42 | 75.56 | 75.33 | 3.18 | 3.12 |
| 42 (OH) | | | 4.60 | 4.44 |
| 43 | 32.99 | 32.99 | 1.76 (eq) 1.17 (ax) | 1.55 (eq) 1.34 (ax) |
| 44 | 30.63 | 30.52 | 1.60 (eq) 0.88 (ax) | 1.60 (eq) 0.88 (ax) |
| 45 | 11.51 | 12.04 | 2.05 | 2.06 |
| 46 | 15.40 | 15.50 | 0.68 | 0.73 |
| 47 | 7.73 | 7.76 | 1.55 | 1.55 |
| 51 | 15.03 | 15.36 | 0.90 | 0.85 |
| 52 | 55.99 | 56.11 | 3.10 | 3.11 |
| 54 | 56.59 | 56.62 | 3.31 | 3.31 |

The pseudo-molecular ions for compound II were observed with the [M−H]$^−$ ion at m/z 706 and fragment ion 424.

For Example 3, $^1$H NMR (DMSO-d$_6$, 400 MHz) δ9.5(1H, —CHO), 6.8 (1H, C═CH), 6.1 (1H, C═CH), 5.07 (1H, OH), 3.88, 3.76, 3.3 (3H, —OCH$_3$), 2.6, 2.2, 1.7, 1.5, 1.4, 1.10, $^{13}$C NMR (DMSO-d$_6$, 100 MHz) δ194.7, 163.5, 131.6, 112.0, 110.4, 81.1, 73.9, 59.0, 35.6, 28.0, 20.3, 14.0. The pseudo-molecular ions for Example 3 were observed with the [M−H]$^−$ ion at m/z 301 and [M+NH4]$^+$ ion at m/z 320 by negative and positive ray modes, respectively.

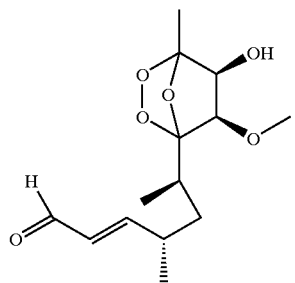

Chemical structure for Example 3, (2E,4S,6R)-6-[(5S,6R)-5-hydroxy-6-methoxy-4-methyl-2,3,7-trioxabicyclo[2.2.1]hept-1-yl]-4-methylhept-2-enal

EXAMPLES 4 AND 5

42-O-(2-Hydroxy)ethyl rapamycin dialdehyde (Example 4) and 42-O-(2-Hydroxy)ethyl rapamycin 29-enol (Example 5)

42-O-(2-hydroxy)ethyl rapamycin (10 mg, 0.01 mmole) was dissolved in 10 mL $CH_2Cl_2$. The round bottom flask was put into a dry ice bath. The ozone gas was bubbling though the solution for 1 min (2 L/min, at output 7 of control knob setting). Then the reaction mixture was stirred 1 h. Methyl sulfide (5 μl) was added and the reaction was stirred for another 0.5 h. About 9 mg of crude product was obtained after work-up. After Preparative HPLC, 0.5 mg of Example 4 was obtained and 0.24 mg of Example 5 was obtained.

The negative ion for Example 4 mode showed the $[M-H]^-$ ion at m/z 988.6. By using rapamycin and 42-O-(2-hydroxy) ethyl rapamycin as internal standards, the exact mass measurement for the unknown ion was 988.5612 Da with elemental composition of $C_{53}H_{82}NO_{16}$ (theoretical mass=988.5634, Δ=2.2 mDa). Example 4 compound contained two more oxygen to compare with 42-O-(2-hydroxy)ethyl rapamycin. Molecular weight was further confirmed by the positive electrospray mode to show a strong $[M+NH4]^+$ ion at m/z 1007.6.

Example 5 showed a pseudo-molecular ion at m/z 769.4 ($[M+NH_4]^+$). The measured exact mass of 769.4487 Da corresponds to the elemental composition of $C_{39}H_{65}N_2O_{13}$ (theoretical mass=769.4487, Δ=0.0 mDa).

What is claimed is:

1. A compound which is a rapamycin 29-enol, said compound having the structure:

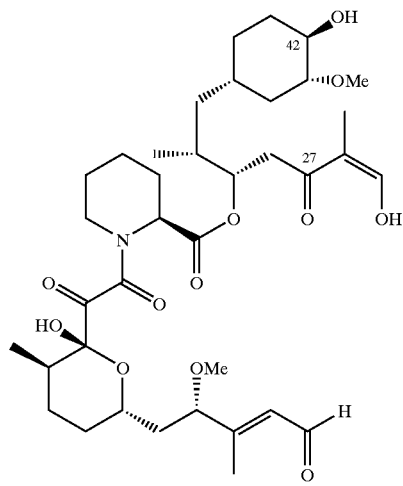

or a pharmaceutically acceptable salt thereof.

2. The compound 42-O-(2-hydroxy)ethyl rapamycin 29-enol.

3. A method of stimulating the growth of damaged peripheral nerves in a mammal in need thereof, which comprises providing said mammal with an effective amount of a rapamycin 29-enol according to claim 1 or 2.

4. A method of treating peripheral nerve damage in a mammal in need thereof, which comprises administering to said mammal an effective amount of a rapamycin 29-enol according to claim 1 or 2.

5. The method according to claim 4 wherein the peripheral nerve damage is caused by a physical injury or trauma.

6. The method according to claim 5, wherein the peripheral nerve damage is caused by spinal cord injury and trauma, sciatic or facial nerve lesion or injury.

7. A method of treating a solid tumor in a mammal in need thereof which comprises providing to said mammal an effective amount of a rapamycin 29-enol according to claim 1 or 2, wherein the solid tumor is selected from the group consisting of astrocytomas, prostate cancer, breast cancer, colon cancer, small cell lung cancer, ovarian cancer; and adult T-cell leukemia/lymphoma.

8. A method of treating or inhibiting a hyperproliferative vascular disorder which comprises providing to said mammal an affective amount of a rapamycin 29-enol according to claim 1 or 2.

9. The method according to claim 8, wherein the rapamycin 29-enol is administered via a vascular stent or shunt.

10. A pharmaceutical composition which comprises a rapamycin 29-enol according to claim 1 or 2 and a pharmaceutical carrier.

* * * * *